United States Patent [19]
Dreikorn

[11] 3,988,455
[45] Oct. 26, 1976

[54] DITETRAZOLO(1,5-A:5',1'-C)QUINOXALINES FOR CONTROL OF SOIL-BORNE PHYTOPATHOGENS

[75] Inventor: Barry A. Dreikorn, Indianapolis, Ind.

[73] Assignee: Eli Lilly and Company, Indianapolis, Ind.

[22] Filed: June 10, 1975

[21] Appl. No.: 585,550

[52] U.S. Cl. ............................................. 424/250
[51] Int. Cl.$^2$ ...................... A01N 9/00; A01N 9/22
[58] Field of Search ................................. 424/250

[56] References Cited
UNITED STATES PATENTS

| | | | |
|---|---|---|---|
| 3,389,137 | 6/1968 | Mosby et al. | 260/256.4 |
| 3,764,681 | 10/1973 | Dreikorn | 424/258 |
| 3,839,569 | 10/1974 | Dreikorn et al. | 424/258 |

*Primary Examiner*—V. D. Turner
*Attorney, Agent, or Firm*—Joseph A. Jones; Everet F. Smith

[57] ABSTRACT

A class of ditetrazolo[1,5-a:5',1'-c]quinoxalines has been found to be useful for protecting plants from soil-borne phytopathogens, such as fusarium root rot, rhizoctonia damping-off and verticillium wilt.

7 Claims, No Drawings

DITETRAZOLO(1,5-A:5',1'-C)QUINOXALINES FOR CONTROL OF SOIL-BORNE PHYTOPATHOGENS

BACKGROUND OF THE INVENTION

This invention belongs to the field of agricultural chemistry, and provides to the art a new method of protecting plants from soil-borne phytopathogens. Such phytopathogens, which cause plant diseases commonly known as wilts and rots, have long been recognized as enemies of crop production. The phytopathogens are to be found in most agricultural soils, and attack germinating seeds and seedlings. Since the damage is done in the soil-buried parts of the plant, it has been particularly difficult to protect plants from such phytopathogens.

A few prior publications are important to the background of this invention. U.S. Pat. Nos. 3,764,681 and 3,839,569, of the present inventor, disclosed the fungicidal efficacy of tetrazolo[1,5-a]quinolines and s-triazolo[4,3-a]quinolines, respectively. Belgian Pat. No. 803,098 and West German Offenlegungsschrift No. 2,249,350 disclosed that certain imidazoquinoxalines were also useful as agricultural fungicides.

SUMMARY OF THE INVENTION

The present invention is a method of reducing the adverse effects of soil-borne phytopathogens, which method comprises contacting the phytopathogens with a compound of the formula

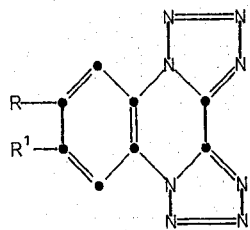

wherein R and $R^1$ independently represent hydrogen, trifluoromethyl, chloro or $C_1$-$C_2$ alkyl.

DESCRIPTION OF THE PREFERRED EMBODIMENT

In the above general formula, the term $C_1$-$C_2$ alkyl refers to methyl and ethyl.

The following exemplary compounds are typical of the compounds used in the invention.
 9-chloroditetrazolo[1,5-a:5',1'-c]quinoxaline
 9,10-dichloroditetrazolo[1,5-a:5',1'-c]quinoxaline
 ditetrazolo[1,5-a:5',1'-c]quinoxaline
 9-chloro-10-methylditetrazolo[1,5-a:5',1'-c]quinoxaline
 9-ethylditetrazolo[1,5-a:5',1'-c]quinoxaline
 9,10-dimethylditetrazolo[1,5-a:5',1'-c]quinoxaline
 9,10-diethylditetrazolo[1,5-a:5',1'-c]quinoxaline
 9-trifluoromethylditetrazolo[1,5-a:5',1'-c]quinoxaline
 9-chloro-10-trifluoromethylditetrazolo[1,5-a:5',1'-c]-quinoxaline
 9-ethyl-10-trifluoromethylditetrazolo[1,5-a:5',1'-c]-quinoxaline It will be understood that the tetrazole moiety of the compounds could be at times in the tautomeric azide form. Spectral evidence indicates that the compounds are primarily in the tetrazole form and remain so under the conditions at which the compounds have usually been handled. However, some conditions of solvent, temperature and pressure could shift the equilibrium to the azide form. Chemists will recognize that the compounds are the same entities, whether they are in the tetrazole or azide form.

The compounds used in this invention are readily obtained by known methods. Some general teaching of the synthesis of the compounds, as well as specific preparative examples, will be given to assure that organic chemists can obtain the compounds. The reader is also referred to Shiho et al., "Studies on Compounds Related to Pyrazine", J. Am. Chem. Soc. 82, 4044–54 (1960), for general discussion of the synthesis.

The starting compounds for the compounds of this invention are appropriately substituted 2,3-dichloroquinoxalines. The starting compounds are obtainable by well-known processes, such as those discussed by Platt, "2-Hydroxy- and 2-Amino-Derivatives of 6- and 7-Methylquinoxaline", J. Chem. Soc., 1310–13 (1948).

In general, the products are formed by the reaction of the 2,3-dichloroquinoxalines with azide ion in aqueous ethanol. Acidifying the reaction mixture often improves the yield. From 1 to 8 hours of the reaction time at the reflux temperature is usually adequate to form the product in high yield.

The starting compounds are most conveniently made by the reaction of an appropriately substituted o-phenylenediamine with an oxalic acid derivative such as the acid halide or ester in ethanol to form a 2,3-quinoxalinedione. (Platt, supra, shows the compound as a quinoxalinol.) The quinoxalinedione is reacted with a chlorinating agent such as $POCl_3$ to form the corresponding 2,3-dichloroquinoxaline intermediate.

The intermediate is dissolved in an alkanol such as ethanol, sodium or potassium azide in water is added, and the reaction is initiated by addition of a strong acid. The reactions proceed in acceptable yields at reflux temperatures. Reaction times in the range of 24–72 hours are required. See Dreikorn, U.S. Pat. No. 3,764,681, for a discussion of the preparation of related tetrazoloquinolines.

The following preparative examples are presented to assure that organic chemists can prepare the compounds.

EXAMPLE 1

9-methylditetrazolo[1,5-a:5',1'-c]quinoxaline

A 16.3 g. portion of 2,3-dichloro-6-methylquinoxaline was dissolved in 10 percent aqueous ethanol, and a saturated aqueous solution of 19.5 g. of sodium azide was added. To the mixture was carefully added, with stirring, 75 ml. of 10 percent aqueous HCl. The stirred mixture was gently refluxed for 72 hours. After cooling, the reaction mixture was evaporated to dryness under vacuum. The solids were washed with water and recrystallized from ethanol to produce 9-methylditetrazolo[1,5-a:5',1'-c]quinoxaline, m.p. 220° C. dec., which was identified by nuclear magnetic resonance analysis and elemental microanalysis, as follows.

|   | Theoretical | Found |
|---|---|---|
| C | 47.79% | 47.49% |

-continued

| | Theoretical | Found |
|---|---|---|
| H | 2.67 | 2.68 |
| N | 49.54 | 49.36 |

EXAMPLE 2

9,10-dichloroditetrazolo[1,5-a:5',1'-c]quinoxaline

Five g. of 2,3,6,7-tetrachloroquinoxaline was suspended in 500 ml. of denatured ethanol, and 8 g. of sodium azide was added. The mixture was stirred at reflux temperature for 72 hours. The product precipitated upon cooling the mixture, and was recovered by filtration. The separated product was washed with water and recrystallized from ethanol to produce 1.2 g. of 9,10-dichloroditetrazolo-[1,5-a:5',1'-c]quinoxaline, m.p. 220° C. dec., which was identified by nuclear magnetic resonance analysis and elemental microanalysis.

| | Theoretical | Found |
|---|---|---|
| C | 34.08% | 34.15% |
| H | 0.71 | 0.87 |
| N | 38.74 | 39.99 |
| Cl | 25.15 | 25.29 |

The compounds described above have been shown in a number of in vivo tests to protect plants from the adverse effects of soil-borne phytopathogens. The following examples illustrate the tests employed and the results produced by representative compounds.

Untreated, infected controls and untreated, normal controls were included in each test. The results are reported on a 1–5 rating scale where 1 indicates severe disease and 5 indicates complete control of the disease. An empty space in the tables below shows that the indicated compound was not tested at the indicated rate. In some cases, more than one test was performed against a given phytopathogen, and the results in such cases are reported as averages.

The following test methods were used.

TEST 1 pythium damping-off test

An aqueous dispersion of each compound to be tested was prepared by first dissolving 114 mg. of the compound in 2 ml. of acetone/ethanol, and then dispersing the solution in about 30 ml. of water containing 0.1 percent of a nonionic surfactant.

Soil was infected with *Pythium aphanidermatum*, the causative organism of pythium damping-off disease, by growing four separate isolates of the organism in cornmeal and adding portions of all four cultures to greenhouse soil which had previously been sterilized to kill wild organisms.

Four ml. of the test compound dispersion was added to 150 g. of infected soil by absorbing the dispersion on granular clay particles and mixing the particles through the soil. The treatment rate was equivalent to 44.8 kg./ha. Lower rates were used in some tests, as shown below. The soil was then transferred to a small plastic pot which was planted with 12 cotton seeds. The pots were watered and placed in a moist growth chamber until the cotton seedlings emerged, when the pots were transferred to the greenhouse for observation. Disease ratings were made 14 days after planting the seed.

TEST 2 fusarium root rot test

The compounds were tested in a procedure essentially similar to the procedure of Test 1, except that the infecting organism was *Fusarium solani* f. phaseoli, the causative organism of fusarium root rot, which was grown in sand mixed with fusarium-infected wheat seed. The host plant was bean, of which three seeds were planted in each pot.

TEST 3 rhizoctonia damping-off test

The test was conducted, in general, according to the method used in the pythium damping-off test. The phytopathogen was *Rhizoctonia solani*, strain 700, which was grown on cornmeal.

TEST 4 verticillium wilt test

This test was performed as was the test described above except that the host plant was tomato seedlings. The phytopathogen was *Verticillium albo-atrum*, strain V3H.

Table 2

| Compound | Appln. Rate kg./ha. | Fusarium Root Rot (bean) | Pythium Damping-off (cotton) | Rhizoctonia Damping-off (cotton) | Verticillium Wilt (tomato) |
|---|---|---|---|---|---|
| ditetrazolo-[1,5-a:5',1'-c]quinoxaline | 44.8 | 3 | 1 | 1 | 3 |
| 9,10-dichloro-ditetrazolo-[1,5-a:5',1'-c]quinoxaline | 44.8 | 4 | 1 | 4 | 1 |
| 9-methyldi-tetrazolo-[1,5-a:5',1'-c]quinoxaline | 44.8 | 3 | 1 | 1 | 1 |
| 9-chlorodi-tetrazolo-[1,5-a:5',1'-c]quinoxaline | 44.8 | 4.3 | 1 | 3 | 1 |
| | 22.4 | 3 | | 1 | |
| | 11.2 | 2 | | 1 | |
| | 5.6 | 1 | | | |

This invention is a method of reducing the adverse effects of soil-borne phytopathogens which comprises contacting the phytopathogens with an effective phytopathogen-inhibiting amount of one of the compounds described above. The method is carried out by applying a compound described above to the soil in which plants grow, where the compound contacts the phytopathogens. Practice of the method does not necessarily kill the contacted phytopathogens. Application of a sufficient amount of a compound of the invention to inhibit the phytopathogens reduces the adverse effects of the phytopathogen, even though only a part of the phytopathogen population may be killed by the compound.

The method is preferably used for protecting plants from *Fusarium solani*, the causative phytopathogen of fusarium root rot. The preferred compounds, with which the method is preferably carried out, are ditetrazolo[1,5-a:5',1'-c]quinoxaline; 9,10-dichloroditetrazolo[1,5-a:5',1'-c]quinoxaline; 9-methylditetrazolo[1,5-a:5',1'-c]quinoxaline; and 9-chloroditetrazolo[1,5-a:5',1'-c]quinoxaline.

As is usual in the plant protection art, best results are obtained by applying the compound several times during the growing season at intervals of from one to a few weeks, depending on the weather and the severity of the disease.

The methods of formulating the compounds and preparing dispersions of the formulations, and the methods of applying dispersions of the compounds to the soil, are entirely conventional in the plant protection art. Some explanation of the methods of application will be given merely to assure that those skilled in the art can carry out the invention without undue experimentation.

It is most meaningful to describe the application rate in terms of the amount of compound applied per unit area of soil. Compound application rates in the range of from about 10 to about 50 kg./ha. are used in the practice of this invention. Application rates higher and lower than the named range will at times be useful, depending upon the severity of the phytopathogenic infection, the weather, which has a strong effect on the vigor of phytopathogens, and the characteristics of the specific compound in use.

The dispersions in which the compounds are applied are most often aqueous suspensions or emulsions prepared from concentrated formulations of the compounds. Such water-suspendible or emulsifiable formulations are either solids usually known as wettable powders or liquids usually known as emulsifiable concentrates. Wettable powders comprise an intimate mixture of the active compound, an inert carrier and surfactants. The concentration of the active compound is usually from about 10 percent to about 90 percent by weight. The inert carrier is usually chosen from among the attapulgite clays, the montmorillonite clays, the diatomaceous earths, or the purified silicates. Effective surfactants, comprising from about 0.5 percent to about 10 percent of the wettable powder, are found among the sulfonated lignins, the condensed naphthalenesulfonates, the naphthalenesulfonates, the alkylbenzenesulfonates, the alkyl sulfates, and nonionic surfactants such as ethylene oxide adducts of alkyl phenol.

Typical emulsifiable concentrates of the compounds comprise a convenient concentration of the compound, such as from about 100 to about 500 g. per liter of liquid, dissolved in an inert carrier which is a mixture of water-immiscible organic solvent and emulsifiers. Useful organic solvents include the aromatics, especially the xylenes, and the petroleum fractions, especially the high-boiling naphthalenic and olefinic portions of petroleum such as heavy aromatic naphtha. Other organic solvents may also be used, such as the terpenic solvents including rosin derivatives, and complex alcohols such as 2-ethoxyethanol. Suitable emulsifiers for emulsifiable concentrates are chosen from the same types of surfactants used for wettable powders.

The compounds can economically and conveniently be applied to the soil in the form of granular formulations. Such formulations, well known to the agricultural chemical art, are prepared by dispersing the compound on an inert carrier of controlled granular character. Most often, the carrier is a coarsely ground clay, such as attapulgite or kaolin clay, having a particle size in the range of from 0.5 to 3 mm. Such granular formulations are easily applied to the soil with applicators which are specially designed to apply accurately controlled amounts of the granular products to the soil.

I claim:
1. A method of reducing the adverse effects of soil-borne fungal phytopathogens which comprises contacting the phytopathogens with an effective phytopathogen-inhibiting amount of a compound of the formula

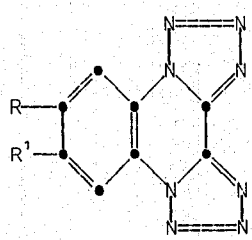

wherein R and R$^1$ independently represent hydrogen, trifluoromethyl, chloro or C$_1$–C$_2$ alkyl.

2. A method of claim 1 in which the amount of the compound is from about 10 to about 50 kg./ha.

3. A method of claim 2 in which the phytopathogen is *Fusarium solani*.

4. The method of claim 1 in which the compound is ditetrazolo[1,5-a:5',1'-c]quinoxaline.

5. The method of claim 1 in which the compound is 9,10-dichloroditetrazolo[1,5-a:5',1'-c]quinoxaline.

6. The method of claim 1 in which the compound is 9-methylditetrazolo[1,5-a:5',1'-c]quinoxaline.

7. The method of claim 1 in which the compound is 9-chloroditetrazolo[1,5-a:5',1'-c]quinoxaline.

* * * * *